(12) United States Patent
Yang

(10) Patent No.: US 11,219,713 B2
(45) Date of Patent: Jan. 11, 2022

(54) DELIVERY SAFETY ENSURING METHOD AND WEARABLE MEDICAL SYSTEM USING THE METHOD

(71) Applicant: MEDTRUM TECHNOLOGIES, INC., Shanghai (CN)

(72) Inventor: Cuijun Yang, Shanghai (CN)

(73) Assignee: Medtrum Technologies, Inc., Shanghai (CN)

( * ) Notice: Subject to any disclaimer, the term of this patent is extended or adjusted under 35 U.S.C. 154(b) by 401 days.

(21) Appl. No.: 16/328,969

(22) PCT Filed: Sep. 27, 2016

(86) PCT No.: PCT/CN2016/100296
§ 371 (c)(1),
(2) Date: Feb. 27, 2019

(87) PCT Pub. No.: WO2018/058287
PCT Pub. Date: Apr. 5, 2018

(65) Prior Publication Data
US 2019/0275234 A1 Sep. 12, 2019

(51) Int. Cl.
*G08B 21/04* (2006.01)
*A61M 5/142* (2006.01)
(Continued)

(52) U.S. Cl.
CPC .... *A61M 5/14244* (2013.01); *A61M 5/14248* (2013.01); *A61M 5/172* (2013.01);
(Continued)

(58) Field of Classification Search
CPC .. G08B 25/006; G08B 25/009; G08B 25/016; G08B 26/00; G08B 26/007; G08B 7/06;
(Continued)

(56) References Cited

U.S. PATENT DOCUMENTS 5,215,334 A * 6/1993 Presson .................. B42D 25/00
283/100
5,739,508 A * 4/1998 Uber, III ............... A61M 5/172
235/375

(Continued)

FOREIGN PATENT DOCUMENTS

| EP | 2001188 A1 | 12/2008 |
|---|---|---|
| WO | WO 2015/179595 A1 | 11/2015 |

OTHER PUBLICATIONS

European Patent Application No. 16917047.9; Extended Search Report; dated Apr. 1, 2020; 9 pages.

*Primary Examiner* — Daniel Previl
(74) *Attorney, Agent, or Firm* — BakerHostetler

(57) ABSTRACT

A delivery safety ensuring method for a wearable delivery system, comprising two major steps to double-ensure that an instruction sent from a smart device trying to control the wearable delivery device reflects the true intention of the user. The first step is to restrict a delivery amount instructed by smart device within a pre-determined range using an alternative physical key, and the second step is to require authentication using an independent authentication tool through proximity communication. Both steps of the safety ensuring method require no open network access, solving the problem of the smart device being vulnerable to program failure and external viruses so as to enhance delivery safety, especially against malicious external attacks from open network. A wearable delivery system using this method is further provided.

14 Claims, 8 Drawing Sheets

(51) Int. Cl.
*G16H 20/10* (2018.01)
*H04W 4/80* (2018.01)
*H04W 76/10* (2018.01)
*A61M 5/172* (2006.01)
*G08B 7/06* (2006.01)
*H04B 1/3827* (2015.01)
*H04W 12/06* (2021.01)
*G16H 20/17* (2018.01)
*G16H 40/63* (2018.01)
*H04W 12/50* (2021.01)
*H04W 12/065* (2021.01)
*H04L 29/08* (2006.01)

(52) U.S. Cl.
CPC .............. *G08B 7/06* (2013.01); *G16H 20/10* (2018.01); *G16H 20/17* (2018.01); *G16H 40/63* (2018.01); *H04B 1/385* (2013.01); *H04B 1/3827* (2013.01); *H04W 4/80* (2018.02); *H04W 12/06* (2013.01); *H04W 12/065* (2021.01); *H04W 12/50* (2021.01); *H04W 76/10* (2018.02); *A61M 2205/18* (2013.01); *A61M 2205/276* (2013.01); *A61M 2205/3375* (2013.01); *A61M 2205/3561* (2013.01); *A61M 2205/3569* (2013.01); *A61M 2205/50* (2013.01); *A61M 2205/582* (2013.01); *A61M 2205/6009* (2013.01); *A61M 2205/609* (2013.01); *A61M 2205/6018* (2013.01); *A61M 2205/6027* (2013.01); *A61M 2205/6045* (2013.01); *A61M 2205/6054* (2013.01); *A61M 2209/01* (2013.01); *A61M 2230/63* (2013.01); *H04L 67/125* (2013.01)

(58) Field of Classification Search
CPC .. H04L 67/12; H04L 67/125; H04M 1/72418; H04M 2242/04; H04M 2242/15; H04M 3/5116; H04W 4/90; H04W 4/80; H04W 12/06; H04W 76/10; H04W 12/003; H04W 12/0605; H04W 12/065; H04W 12/50; A61M 2205/18; A61M 2205/276; A61M 2205/3375; A61M 2205/3561; A61M 2205/3569; A61M 2205/50; A61M 2205/582; A61M 2205/6009; A61M 2205/6018; A61M 2205/6027; A61M 2205/6045; A61M 2205/6054; A61M 2205/609; A61M 2209/01; A61M 2230/63; A61M 5/14244; A61M 5/14248; A61M 5/172; G16H 20/10; G16H 20/17; G16H 40/63; H04B 1/3827; H04B 1/385
USPC ........ 340/539.12, 454, 539.11, 539.1, 568.1, 340/573.1, 691.6, 5.86
See application file for complete search history.

(56) References Cited

U.S. PATENT DOCUMENTS

| | | | |
|---|---|---|---|
| 9,391,670 B2 | 7/2016 | Brukalo et al. | |
| 2014/0153719 A1* | 6/2014 | Kalpin | H04L 63/0428 380/255 |
| 2015/0002425 A1* | 1/2015 | Lee | G06F 3/046 345/173 |
| 2015/0195401 A1* | 7/2015 | Shim | H04L 61/307 455/414.1 |
| 2016/0199572 A1 | 7/2016 | Yang | |
| 2016/0245665 A1 | 8/2016 | Logan et al. | |
| 2017/0124853 A1* | 5/2017 | Mehta | G08B 25/009 |
| 2017/0202722 A1* | 7/2017 | Lei | G02B 27/017 |

* cited by examiner

DELIVERY SAFETY ENSURING METHOD AND WEARABLE MEDICAL SYSTEM USING THE METHOD

CROSS-REFERENCE TO RELATED APPLICATIONS

This application is the National Stage of International Patent Application No. PCT/CN2016/100296 filed Sep. 27, 2016, the disclosure of which is incorporated herein by reference in its entirety.

TECHNICAL FIELD

The present invention generally relates to the field of medical appliance, specifically to a delivery safety ensuring method and a wearable medical system using this method.

BACKGROUND OF THE INVENTION

Smart phones have been becoming more and more indispensable in the modern life, and the trend of making the mobile applications the universal solution for everything is irreversible. Referring to wearable medical devices, running an application to control the medical device using a smart phone with every other function instead of using an additional handset device with no other function is much more convenient and preferred by users with no doubt. But the safety of the communication between the medical device and the smart phone is a big concern. As a price paid for the unprecedented convenience, compromise in the safety of using the smart-phone-controlling medical device is a collateral damage. Because the smart phone has access to the Internet, it is vulnerable to program failure caused by external viruses or malicious external attacks, making the instructions from the smart phone to the medical device untrustworthy, resulting in possible threat to the health and even life safety of the user. However, measures for establishing secure communications between a wearable medical device and a smart phone using mainstream wireless communication techniques are limited.

Pressing the physical buttons set on the wearable medical device for confirmation of the instructions from the smart phone provides one solution, but it requires the user to roll up her or his clothes causing inconvenience. In other solutions such as transmitting encrypted information regarding an encryption key as disclosed in US2014153719A1, or generating a PIN code by the medical device for a user to input in a controlling device as disclosed in EP2001188A1, or generating a communication using the NFC protocol between the medical device and a remote controller as disclosed in U.S. Pat. No. 9,391,670B2, the problem of the vulnerability of the medical device to unauthorized or unintended instructions from the open network remains because all these authentication or identification measures involve devices accessing an open network. For that reason, proximity telemetry communication between the medical device and an external device with no Internet access is applied which greatly enhances the safety of delivery, but due to the immense impact a delivery device may have on human health, additional ensuring method is still required.

SUMMARY OF THE INVENTION

To overcome shortcomings in the prior art mentioned above, one purpose of the present invention is to provide a delivery safety ensuring method involving two major steps using alternative physical keys and independent authentication tools, comprising:

Selecting and inserting an alternative physical key carrying a proper operating mode configured to restrict a delivery amount within a pre-determined range into a wearable medical device by a user;

Determining, via a processor, whether a delivery instruction given by a smart device is within the pre-determined range of the selected physical key by the wearable medical device;

Requiring, via the processor, for authentication of the delivery instruction or a suspension instruction from the smart device by the wearable medical device;

Using an authentication tool independent of the smart device to send an authentication information to a receiver set in the wearable medical device by the user, wherein the communication between the authentication tool and the receiver is a proximity communication without any direct physical contact being needed;

Establishing, via the processor, a secure communication with the smart device by the wearable medical device if the requirement for authentication is satisfied;

Instructing, via the processor, an alert system set in the wearable medical device to give a feedback to the user if the requirement for authentication is satisfied.

Alternatively, the delivery safety ensuring method further comprises declining, via the processor, to establish a secure communication between the smart device and the wearable medical device if the delivery instruction from the smart device is out of the pre-determined range of the selected physical key, or the requirement for authentication is unsatisfied.

Alternatively, the authentication tool is a portable item without Internet access or a movement made by the user.

Alternatively, the receiver is a built-in sensor set in the wearable medical device.

Alternatively, the receiver is a magnetic sensor, and the authentication tool is a portable item made of or containing magnetic material.

Alternatively, the authentication tool is a portable item made of or containing metal material, and the receiver is one of a capacitive sensor, an inductive sensor and an eddy-current sensor.

Alternatively, the receiver is a linear accelerometer, and the authentication tool is a linear movement made by the user which is one or a combination of jumping, squatting and tapping the wearable medical device through clothing.

Alternatively, the receiver is a gyroscope sensor, and the authentication tool is a twisting movement made by the user.

Alternatively, the receiver is an ultrasonic receiving sensor, and the authentication tool is a portable item with an ultrasonic transmitter.

Alternatively, the receiver is a built-in RFID reader or tag, and the authentication tool is a portable item with a corresponding RFID tag or reader.

Alternatively, the receiver is a built-in NFC reader or tag, and the authentication tool is a portable item with a corresponding NFC tag or reader.

Alternatively, the alert system set in the wearable medical device comprises a buzzer and a vibration motor.

Alternatively, the operating mode comprises one or a combination of a basal rate delivery mode, a programmable basal rate delivery mode, a bolus dose delivery mode, a delivery suspension mode, a system locking mode and a wireless control mode.

The other purpose of the present invention is to provide a wearable medical system using the above-identified delivery safety ensuring method, comprising a delivery device which comprises a processor, a receiver, an alert system and alternative physical keys with respective operating modes; as well as an authentication tool independent of a smart device, with all the components functioning as mentioned in the delivery safety ensuring method.

Alternatively, the alternative physical keys further carry pre-determined setting rules, configured to limit acceptable orders to changing system settings or executing special instructions from the smart device.

Compared to prior arts, the present invention has advantages in the following ways: Firstly, the alternative physical keys are designed with pre-determined operating modes which restrict the amounts of drug fluid to be delivered to the user within a certain range independent of the instructions from a smart phone, so an instruction of delivery amount out of the pre-determined range of an alternative physical key selected and inserted into the wearable medical device by the user will not be accepted by the processor and no active communication between the medical device and the smart phone would be established. Due to the reason that the alternative physical keys have no access to open network, there is hardly a chance of them being invaded by external viruses. Secondly, when a delivery amount of an instruction from the smart phone fits in the restricted range of a selected physical key, the processor requests for a further safety ensuring measure and an independent third-party item or movement is involved as an authentication tool. If the requirement of authentication is satisfied, a secure communication of the medical device and the smart phone will eventually be established. Since the independent authentication tool communicates with the receiver in the medical device using proximity communication which requires no open network access, this way of authentication further enhances the safety of the delivery, especially against malicious external attack via network. Last but not least, the proximity communication applying electric or magnetic field, NFC or RFID protocol, a linear or twisting movement which can be sensed by an accelerometer or a gyroscope requires no rolling up clothes of the user, which improves the convenience of using the wearable medical device by both protecting the user's privacy and keeping the user warm.

DETAILED DESCRIPTION

To make the above-mentioned objects, features and advantages of the present invention more obvious and understandable, the embodiments of the present invention are described in the following through specific embodiments.

Figure 1:
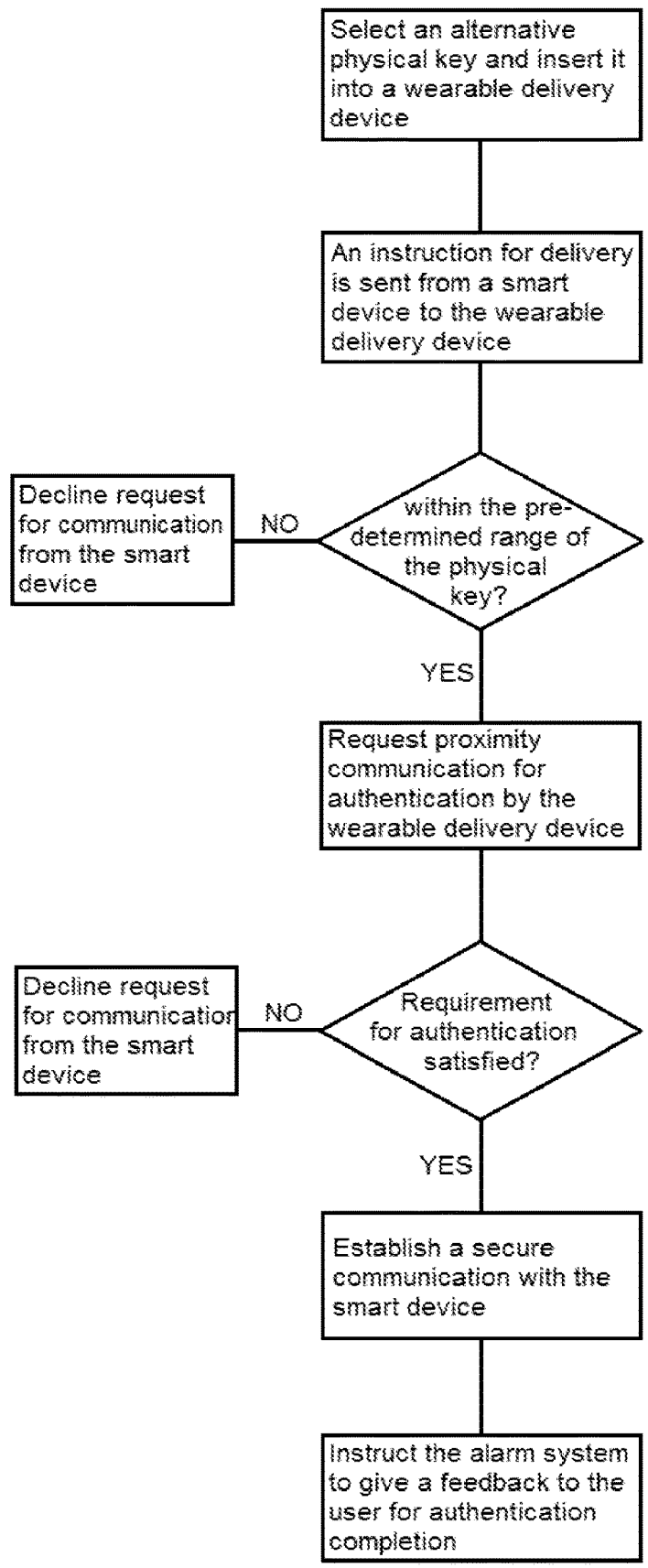
FIG. 1 is a flow diagram of the complete delivery safety ensuring method of the present invention

FIG. 1 shows the complete method to ensure delivery safety in the present invention, comprising two major steps to double-ensure an instruction sent from a smart device trying to control the wearable delivery device reflects the user's true intention.

Figure 2:
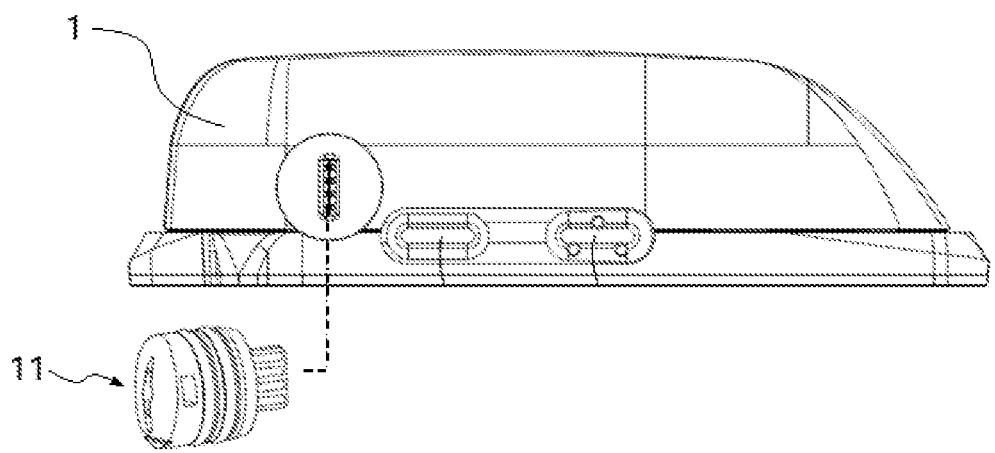
FIG. 2 is a schematic diagram of how an alternative physical key is connected to a wearable medical device

First of all, the user should select an alternative physical key 11 with a proper operating mode which restricts the available delivery amount within a pre-determined range, and insert the selected physical key 11 into a socket of the wearable delivery device 1 as shown in FIG. 2. The operating mode of an alternative physical key 11 comprises one or a combination of a basal rate delivery mode, a programmable basal rate delivery mode, a bolus dose delivery mode, a delivery suspension mode, a system locking mode and a wireless control mode. When a delivery instruction is sent from the smart device, the wearable delivery device 1 will determine, via a processor, whether the delivery instruction is within the pre-determined range of the selected physical key. If an instruction from a smart device requires a delivery of an amount out of the pre-determined range of the physical key 11 selected by the user, the processor of the wearable delivery device 1 will decline to establish a secure communication with the smart device. So even if the smart device of the user's is hacked and tries to instruct the wearable delivery device 1 to deliver a lethal dose to the user, it will not work.

If an instruction from the smart device requires a delivery amount within the pre-determined range of the selected physical key 11, the wearable delivery device 1 will further require, via the processor, authentication of the delivery instruction or a suspension instruction from the smart device using proximity communication.

At this step, the user should use an authentication tool independent of the smart device to send authentication information to a receiver set in the wearable delivery device. It may require a small effort of the user to carry a portable item wherever she or he is wearing the delivery device, but an independent tool without open network access is certainly much safer than the smart device itself, so carrying a compact and lightweight item for authentication use is strongly suggested for safety reasons.

Figure 3:
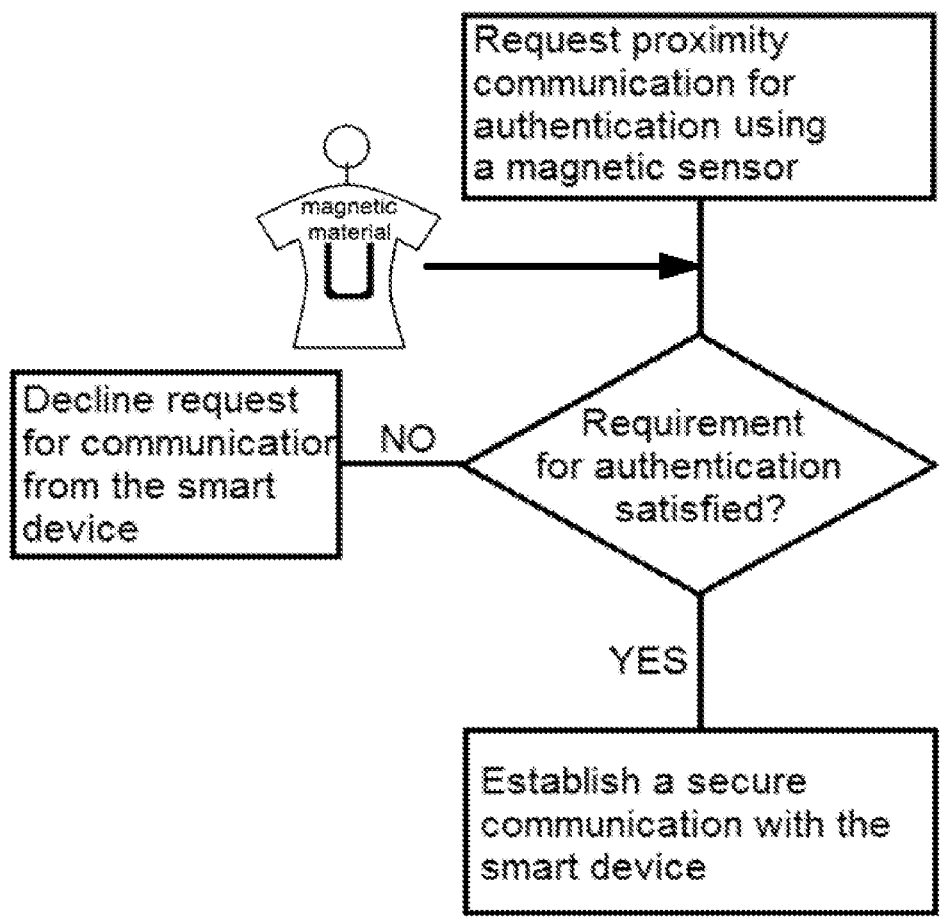
FIG. 3-11 are flow diagrams of representative methods of the proximity communication for authentication in the present invention

Referring to FIG. 3, an embodiment of proximity authentication using a built-in sensor in the present invention is provided. In this embodiment, the portable item is a key chain with a magnet, and the built-in sensor is a magnetic sensor. When the processor of the delivery device requires authentication, the user should put the key chain near the delivery device, and the built-in magnetic sensor in the delivery device will sense the magnetic field, so the authentication will be completed, and a secure communication between the smart device and the wearable delivery device will be established. During this process, it is not necessary for the user to roll up her or his clothes to operate the wearable delivery device directly, which makes the authentication convenient. If the instruction from the smart device is not from the user, no authentication information will be sent to the built-in sensor, and no secure communication between the smart device and the wearable delivery device can be established, resulting in no delivery or suspension instruction being executed.

Figure 4:
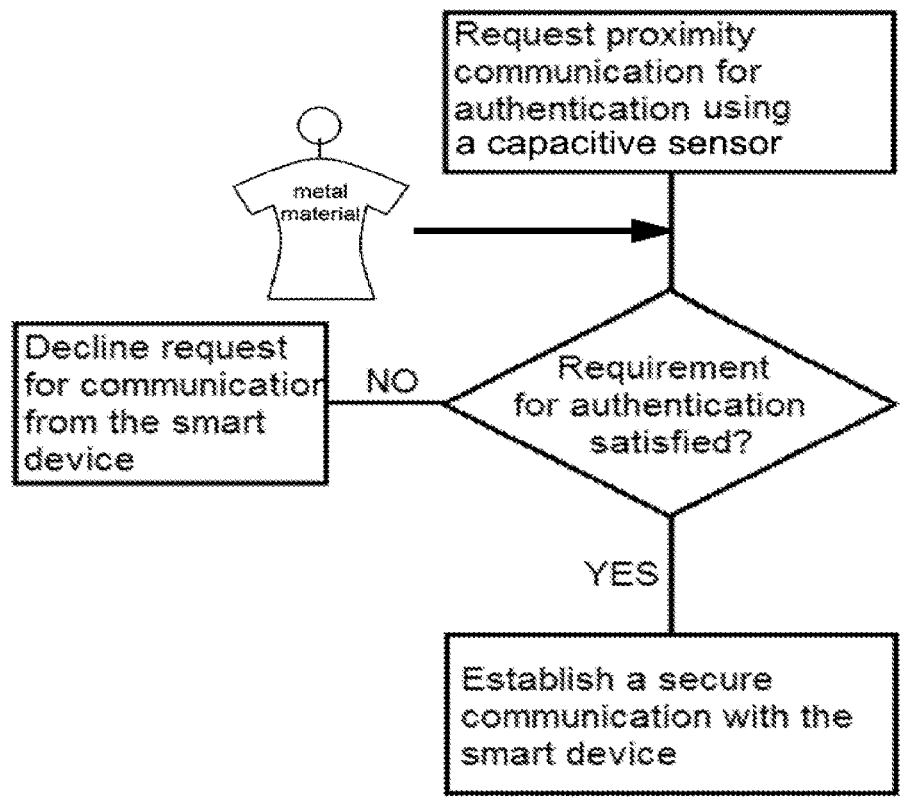
Figure 5:
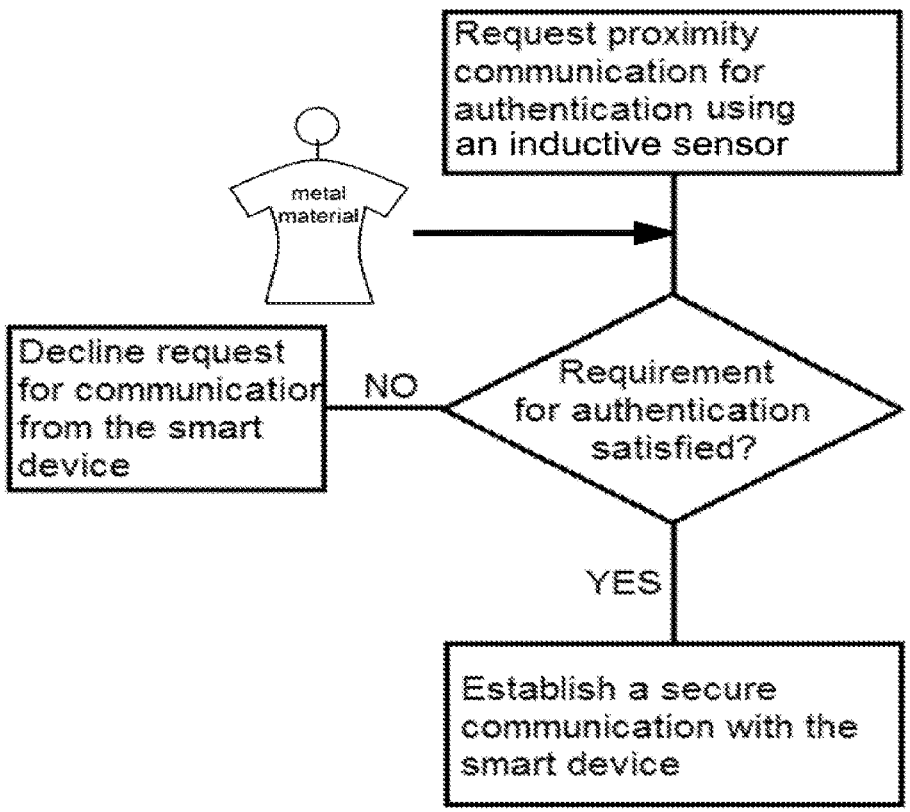
Figure 6:
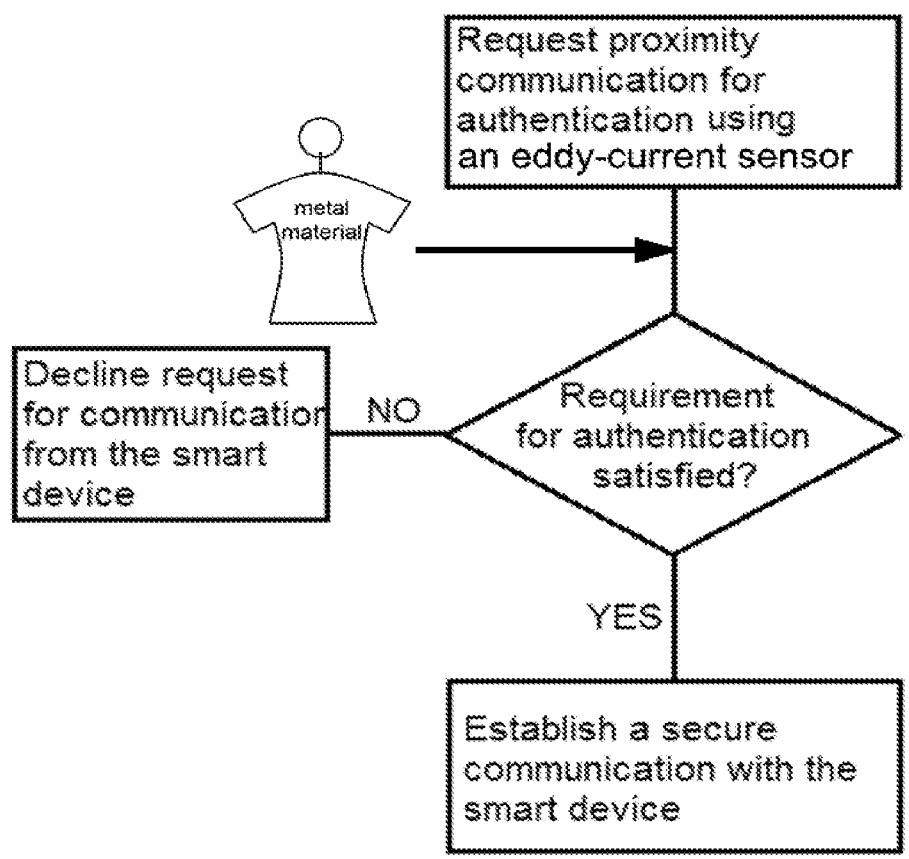

Referring to FIG. 4-6, an embodiment of proximity authentication using a built-in sensor in the present invention is provided. In this embodiment, the portable item is a key chain with or made of metal material, and the built-in sensor is a capacity, inductive, or eddy-current sensor. When the processor of the delivery device requires authentication, the user should put the key chain near the delivery device, and the built-in metal sensor in the delivery device will sense the electric field, so the authentication will be completed, and a secure communication between the smart device and the wearable delivery device will be established. During this process, it is not necessary for the user to roll up her or his clothes to operate the wearable delivery device directly, which makes the authentication convenient. If the instruction from the smart device is not from the user, no authentication information will be sent to the built-in sensor, and no secure communication between the smart device and the wearable delivery device can be established, resulting in no delivery or suspension instruction being executed.

Figure 7:
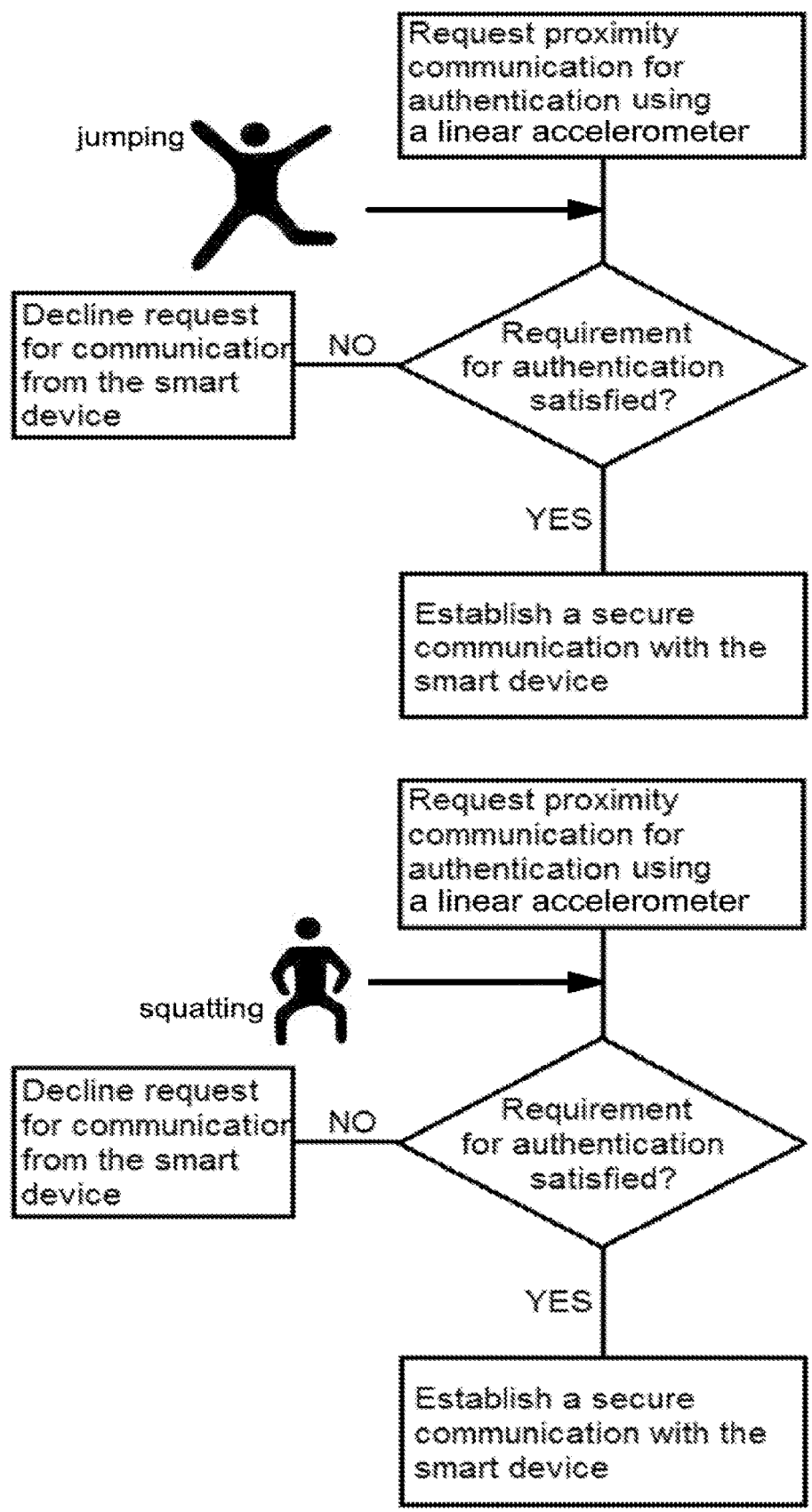
Figure 8:
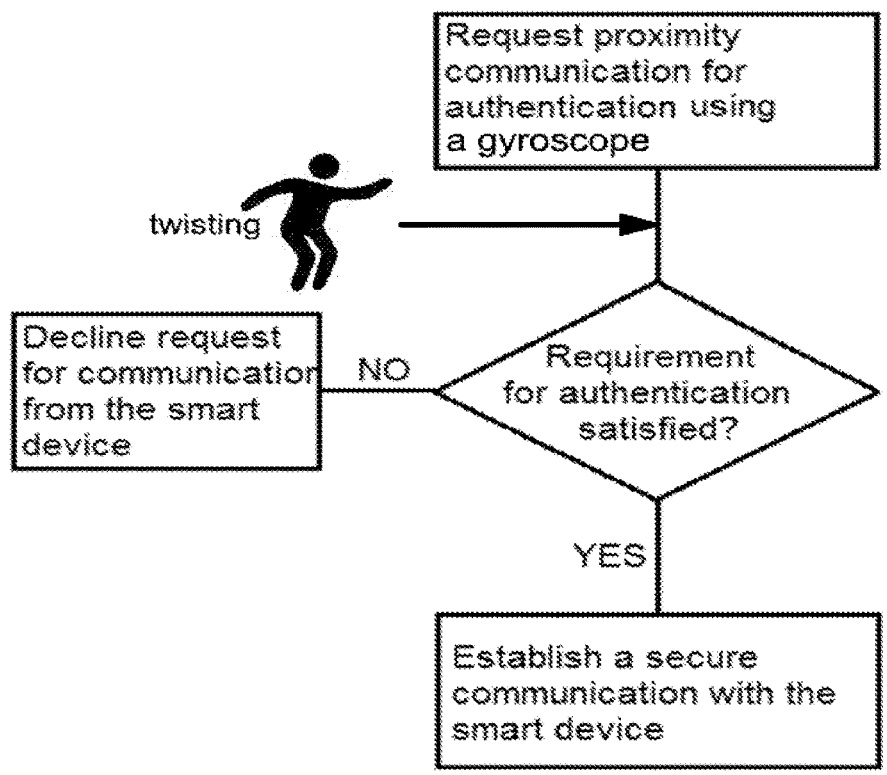

Referring to FIGS. 7 and 8, an embodiment of proximity authentication using a built-in sensor in the present invention is provided. In this embodiment, the authentication tool is a movement made by the user, and the built-in sensor is a linear accelerometer in FIG. 7 or a gyroscope in FIG. 8. When the processor of the delivery device requires authentication, the user should make a linear movement like jumping or squatting in FIG. 7, or a twisting movement like twisting her or his body clockwise in FIG. 8, and the built-in accelerometer or a gyroscope in the delivery device will sensor the linear or angular acceleration, so the authentication will be completed, and a secure communication between the smart device and the wearable delivery device will be established. If the instruction from the smart device is not from the user, no authentication information will be sent to the built-in sensor, and no secure communication between the smart device and the wearable delivery device can be established, resulting in no delivery or suspension instruction being executed.

Figure 9:
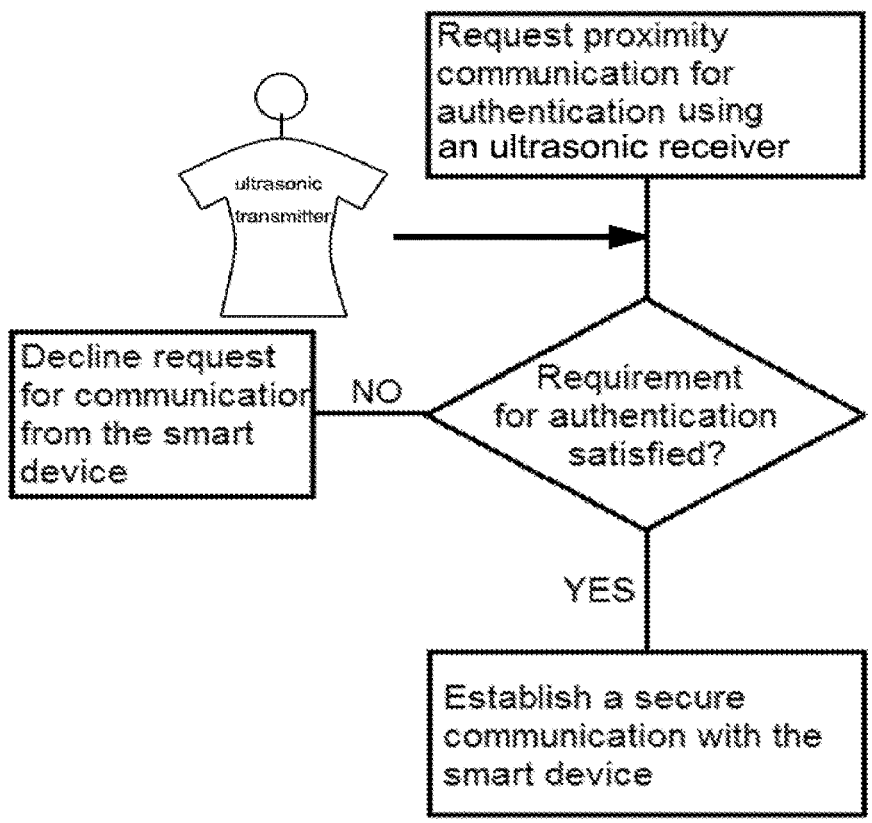

Referring to FIG. 9, an embodiment of proximity authentication using a built-in sensor in the present invention is provided. In this embodiment, the portable item is a key chain with an ultrasonic transmitter, and the built-in sensor is an ultrasonic receiver. When the processor of the delivery device requires authentication, the user should put the key chain near the delivery device, and the built-in ultrasonic receiver in the delivery device will sense the ultrasonic wave, so the authentication will be completed, and a secure communication between the smart device and the wearable delivery device will be established. During this process, it is not necessary for the user to roll up her or his clothes to operate the wearable delivery device directly, which makes the authentication convenient. If the instruction from the smart device is not from the user, no authentication information will be sent to the built-in ultrasonic receiver, and no secure communication between the smart device and the wearable delivery device can be established, resulting in no delivery or suspension instruction being executed.

Figure 10:
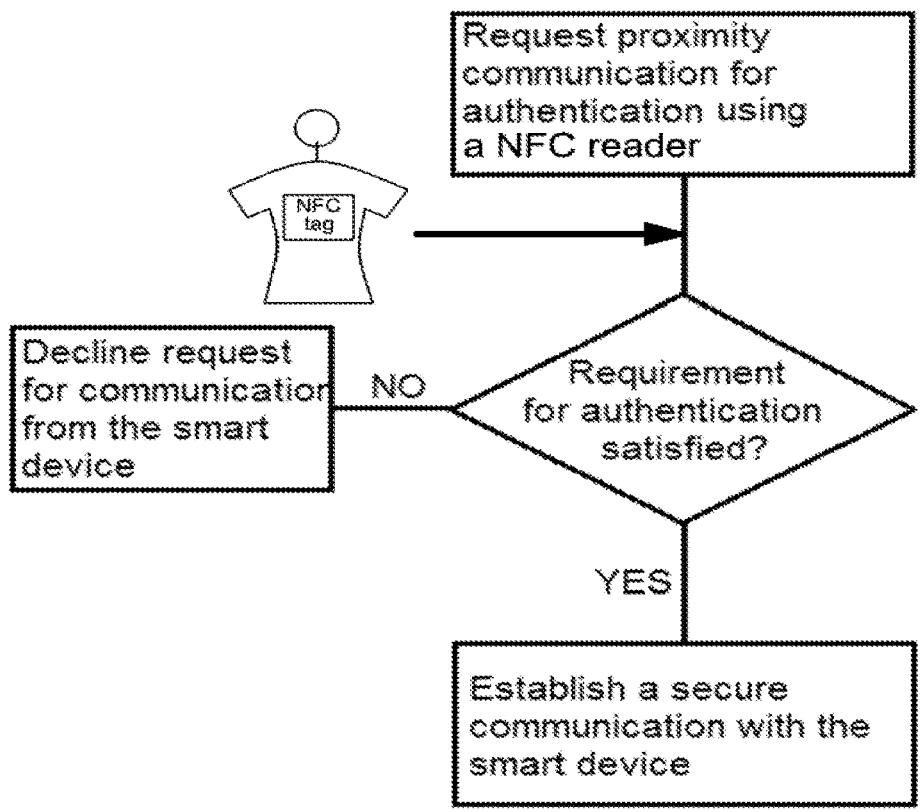

Referring to FIG. 10, an embodiment of proximity authentication based on NFC protocol in the present invention is provided. In this embodiment, the portable item is a key chain with an NFC tag, and an NFC reader is set in the wearable delivery device. When the processor of the delivery device requires authentication, the user should put the key chain near the delivery device, and the NFC reader in the delivery device will sense the near-field communication using NFC protocol, so the authentication will be completed, and a secure communication between the smart device and the wearable delivery device will be established. During this process, it is not necessary for the user to roll up her or his clothes to operate the wearable delivery device directly, which makes the authentication convenient. If the instruction from the smart device is not from the user, no authentication information will be sent to the NFC reader, and no secure communication between the smart device and the wearable delivery device can be established, resulting in no delivery or suspension instruction being executed. In this embodiment, it is the NFC reader that is set in the wearable delivery device, and the NFC tag is carried by the authentication tool, but obviously, the two are interchangeable.

Figure 11:
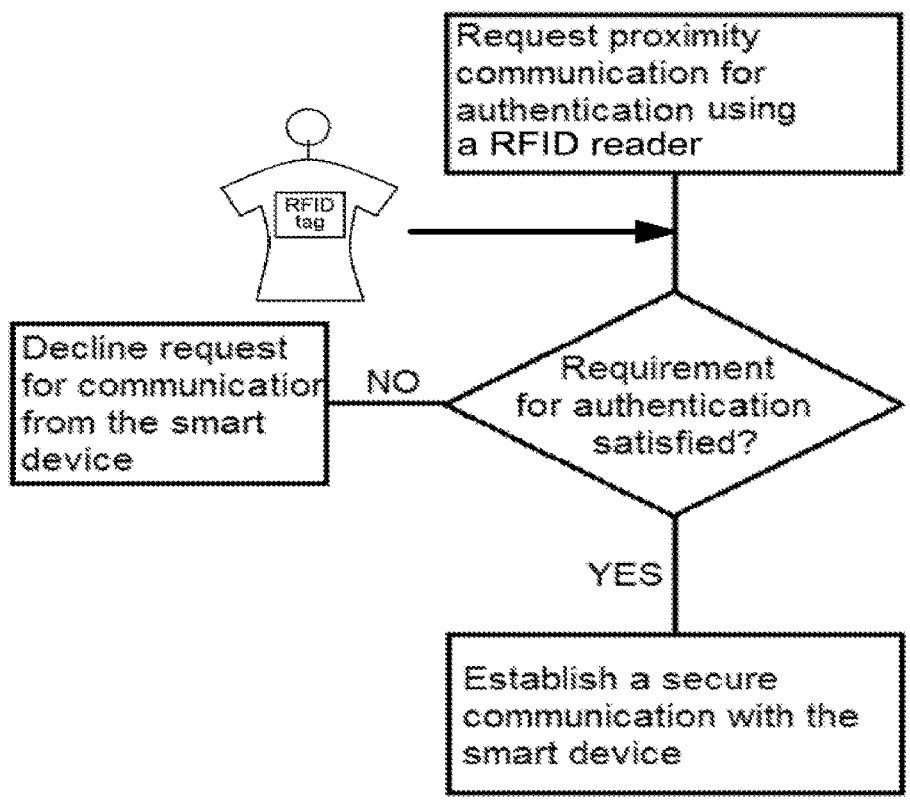

Referring to FIG. 11, an embodiment of proximity authentication based on RFID technology in the present invention is provided. In this embodiment, the portable item is a key chain with an RFID tag, and an RFID reader is set in the wearable delivery device. When the processor of the delivery device requires authentication, the user should put the key chain near the delivery device, and the RFID reader in the delivery device will sense the proximity communication using radio frequency identification technology, so the authentication will be completed, and a secure communication between the smart device and the wearable delivery device will be established. During this process, it is not necessary for the user to roll up her or his clothes to operate the wearable delivery device directly, which makes the authentication convenient. If the instruction from the smart device is not from the user, no authentication information will be sent to the RFID reader, and no secure communication between the smart device and the wearable delivery device can be established, resulting in no delivery or suspension instruction being executed. In this embodiment, it is the RFID reader that is set in the wearable delivery device, and the RFID tag is carried by the authentication tool, but obviously, the two are interchangeable.

Figure 12:
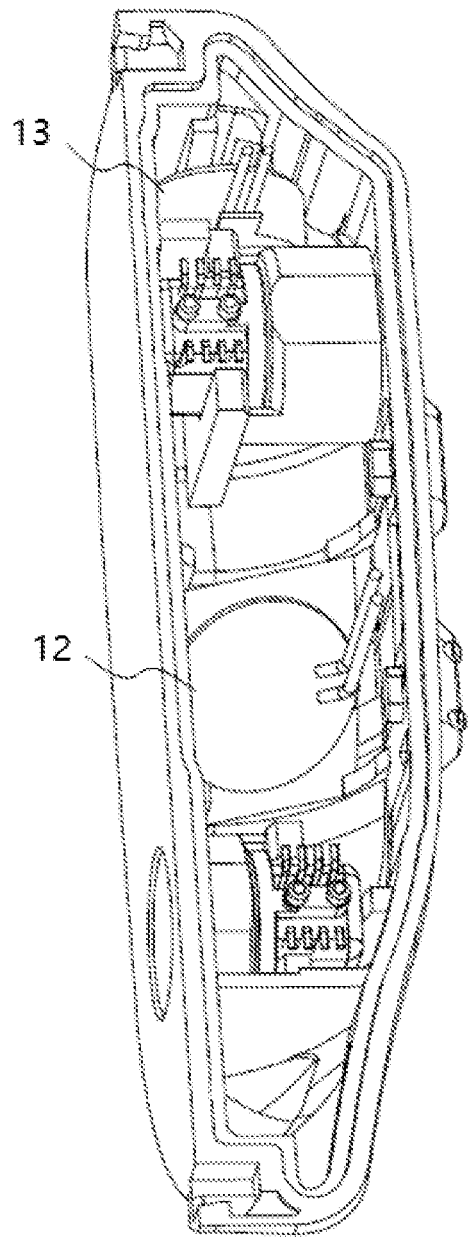
FIG. 12 is a schematic diagram of an alert system of the wearable medical device in the present invention.

Referring to FIG. 12, an embodiment of an alert system in the present invention is provided. When a requirement for authentication is satisfied using proximity communication, a secure communication between the smart device and the wearable delivery device is established, meaning the instruction from the smart device is accepted by the wearable delivery device, and the wearable delivery device will instruct, via the processor, an alert system to give a feedback to the user. As shown in FIG. 12, the alert system comprises a buzzer 12 and a vibration motor 13 set in the wearable delivery device. When a requirement for authentication is satisfied, the buzzer 12 will beep, or the vibration motor 13 will vibrate, or both, to remind the user the authentication for safe delivery is completed, the delivery instruction from the smart device can be safely executed.

The present invention further provides a wearable medical system using the above-identified delivery safety ensuring method. The wearable medical system comprises a delivery device comprising a processer, a receiver, an alert system and alternative physical keys with respective operating modes; as well as an authentication tool independent of a smart device, with all the components functioning as mentioned above in the delivery safety ensuring method.

In a preferred embodiment, the alternative physical keys of the wearable medical system further carry pre-determined setting rules, configured to limit acceptable orders to changing system settings or executing special orders from the smart device, such as altering alert or alarm thresholds.

The above descriptions of the detailed embodiments are only to illustrate the principle and the effect of the present invention, and it is not to limit the scope of the present invention. Those skilled in the art can modify or change the embodiments without departing from the spirit and scope of the present invention. Accordingly, all equivalent modifications and variations completed by persons of ordinary skill in the art, without departing from the spirit and technical idea of the present invention, should fall within the scope of the present disclosure defined by the appended claims.

The invention claimed is:

1. A delivery safety ensuring method for a wearable medical system, comprising the following steps:

1) selecting and inserting an alternative physical key into a wearable medical device by a user, wherein the alternative physical key is carrying a proper operating mode configured to restrict a delivery amount within a pre-determined range;
2) determining, via a processor, whether a delivery instruction given by a smart device is within the pre-determined range of the selected physical key by the wearable medical device;
3) requiring, via the processor, for authentication of the delivery instruction or a suspension instruction from the smart device by the wearable medical device;
4) using an authentication tool independent of the smart device to send an authentication information to a receiver set in the wearable medical device by the user, wherein the communication between the authentication tool and the receiver is a proximity communication without any direct physical contact being needed;
5) establishing, via the processor, a secure communication with the smart device by the wearable medical device if the requirement for authentication is satisfied;
6) instructing, via the processor, an alert system set in the wearable medical device to give a feedback to the user if the requirement for authentication is satisfied wherein if the delivery amount is out of the pre-determined range, the processor will decline to establish a secure communication between the smart device and the wearable medical device; and if the delivery amount is within the pre-determined range, the processor requests for a further safety ensuring measure using the authentication tool independent of the smart device; and if the requirement for authentication is unsatisfied, the processor will decline to establish a secure communication between the smart device and the wearable medical device.

2. The delivery safety ensuring method for a wearable medical system according to claim 1, wherein,
the authentication tool is a portable item without Internet access or a movement made by the user.

3. The delivery safety ensuring method for a wearable medical system according to claim 1, wherein,
the receiver is a built-in sensor set in the wearable medical device.

4. The delivery safety ensuring method for a wearable medical system according to claim 3, wherein,
the receiver is a magnetic sensor, and the authentication tool is a portable item made of or containing magnetic material.

5. The delivery safety ensuring method for a wearable medical system according to claim 3, wherein,
the authentication tool is a portable item made of or containing metal material, and the receiver is one of a capacitive sensor, an inductive sensor and an eddy-current sensor.

6. The delivery safety ensuring method for a wearable medical system according to claim 3, wherein,
the receiver is a linear accelerometer, and the authentication tool is a linear movement made by the user which is one or a combination of jumping, squatting and tapping the wearable medical device through clothing.

7. The delivery safety ensuring method for a wearable medical system according to claim 3, wherein,
the receiver is a gyroscope sensor, and the authentication tool is a twisting movement made by the user.

8. The delivery safety ensuring method for a wearable medical system according to claim 3, wherein,
the receiver is an ultrasonic receiving sensor, and the authentication tool is a portable item with an ultrasonic transmitter.

9. The delivery safety ensuring method for a wearable medical system according to claim 1, wherein,
the receiver is a built-in RFID reader or tag, and the authentication tool is a portable item with a corresponding RFID tag or reader.

10. The delivery safety ensuring method for a wearable medical system according to claim 1, wherein,
the receiver is a built-in NFC reader or tag, and the authentication tool is a portable item with a corresponding NFC tag or reader.

11. The delivery safety ensuring method for a wearable medical system according to claim 1, wherein,
the alert system set in the wearable medical device comprises a buzzer and a vibration motor.

12. The delivery safety ensuring method for a wearable medical system according to claim 1, wherein,
the operating mode comprises one or a combination of a basal rate delivery mode, a programmable basal rate delivery mode, a bolus dose delivery mode, a delivery suspension mode, a system locking mode and a wireless control mode.

13. A wearable medical system, comprising,
a delivery device comprising a processor, a receiver, an alert system and alternative physical keys with respective operating modes;
an authentication tool independent of a smart device;
wherein the wearable medical system uses the delivery safety ensuring method according to claim 1.

14. A wearable medical system according to claim 13, wherein,
the alternative physical keys further carry pre-determined setting rules, configured to limit acceptable orders to changing system settings or executing special instructions from the smart device.

* * * * *